United States Patent [19]

Cai et al.

[11] Patent Number: 6,051,707
[45] Date of Patent: Apr. 18, 2000

[54] LINEAR PROCESS FOR THE PREPARATION OF A MORPHOLINE COMPOUND

[75] Inventors: Dongwei Cai, Edison; Michel Journet, Somerset; Robert D. Larsen, Bridgewater, all of N.J.

[73] Assignee: Merck & Co., Inc., Rahway, N.J.

[21] Appl. No.: 09/428,315

[22] Filed: Oct. 28, 1999

Related U.S. Application Data

[60] Provisional application No. 60/106,289, Oct. 30, 1998.
[51] Int. Cl.[7] .................................................. C07D 413/06
[52] U.S. Cl. ............................................................ 544/132
[58] Field of Search ............................................... 544/132

[56] References Cited

U.S. PATENT DOCUMENTS 5,612,337   3/1997   Baker et al. ........................ 514/236.2

*Primary Examiner*—Robert W. Ramsuer
*Attorney, Agent, or Firm*—J. Eric Thies; David L. Rose

[57] ABSTRACT

The present invention is concerned with a novel linear process for the preparation of 2-(R)-(1-(R)-(3,5-bis(trifluoromethyl) phenyl)-ethoxy)-4-(5-(dimethylamino)methyl-1,2,3-triazol-4-yl)methyl-3-(S)-(4-fluorophenyl)-morpholine which is a potent and selective substance P (or neurokinin-1) receptor antagonist usefull as a therapeutic agent.

16 Claims, No Drawings

LINEAR PROCESS FOR THE PREPARATION OF A MORPHOLINE COMPOUND

This application claims priority from U.S. Ser. No. 60/106,289, filed Oct. 30, 1998.

BACKGROUND OF THE INVENTION

The present invention relates to processes for the preparation of 2-(R)-(1-(R)-(3,5-bis(trifluoromethyl)phenyl) ethoxy)-4-(5-(dimethyl-amino)methyl-1,2,3-triazol-4-yl) methyl-3-(S)-(4-fluorophenyl)morpholine which is useful as a therapeutic agent.

The compound 2-(R)-(1-(R)-(3,5-bis(trifluoromethyl) phenyl)-ethoxy)-4-(5-(dimethylamino)methyl-1,2,3-triazol-4-yl)methyl-3-(S)-(4-fluorophenyl)-morpholine is a potent and selective substance P (or neurokinin-1) receptor antagonist. Substance P antagonists have potential for use in the treatment of inflammatory diseases, emesis, depresssion, anxiety, and other neuropsychiatric diseases, including bipolar disorder and schizophrenia.

U.S. Pat. No. 5,612,337 describes the preparation of 2-(R)-(1-(R)-(3,5-bis(trifluoromethyl)phenyl)-ethoxy)-4-(5-(dimethylamino)methyl-1,2,3-triazol-4-yl)methyl-3-(S)-(4-fluorophenyl)morpholine which has the structure:

by a four step process starting from 2-(R)-(1-(R)-(3,5-bis (trifluoromethyl)-phenyl)-ethoxy)-3-(S)-(4-fluorophenyl) morpholine. With reference to Example 12, Method A, of U.S. Pat. No. 5,612,337, the compound is prepared as follows:

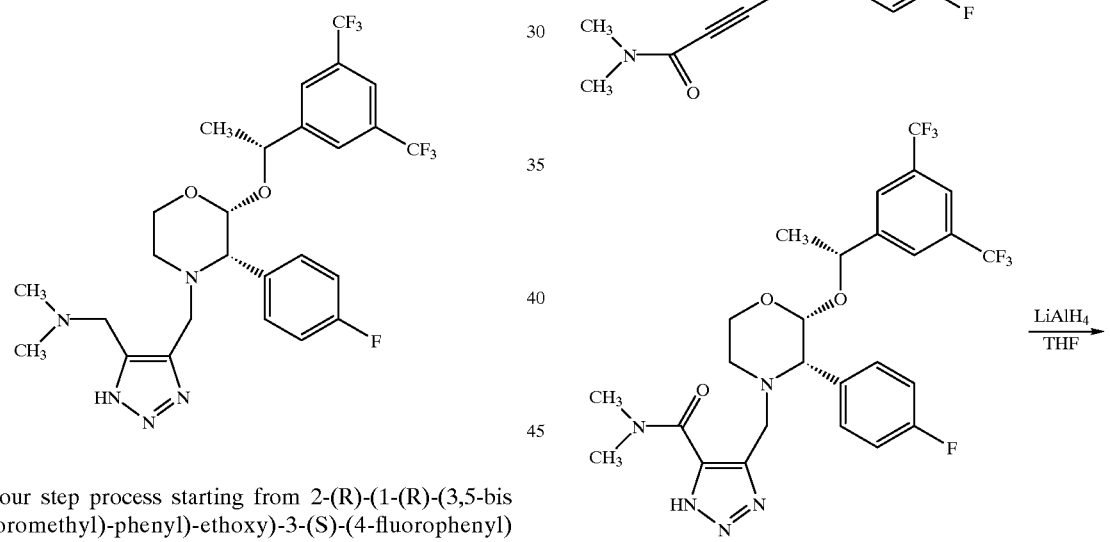

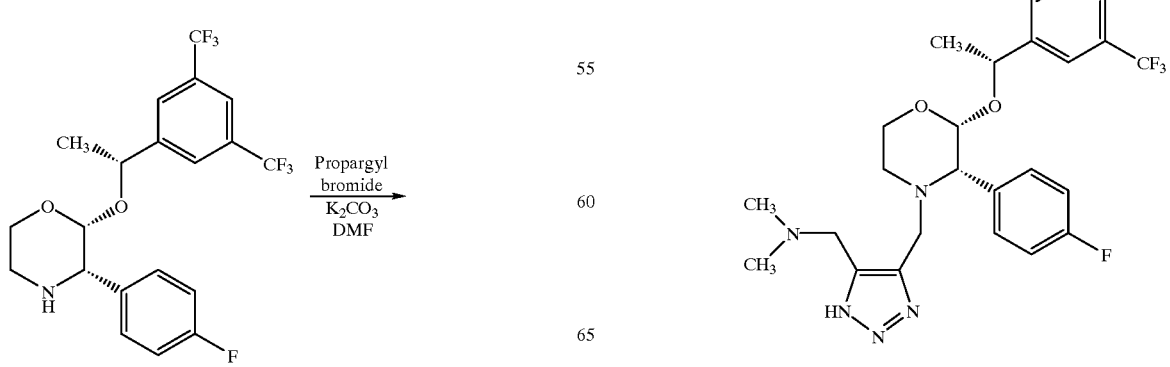

With reference to Example 12, Method B, of U.S. Pat. No. 5,612,337, the compound is also prepared as follows:

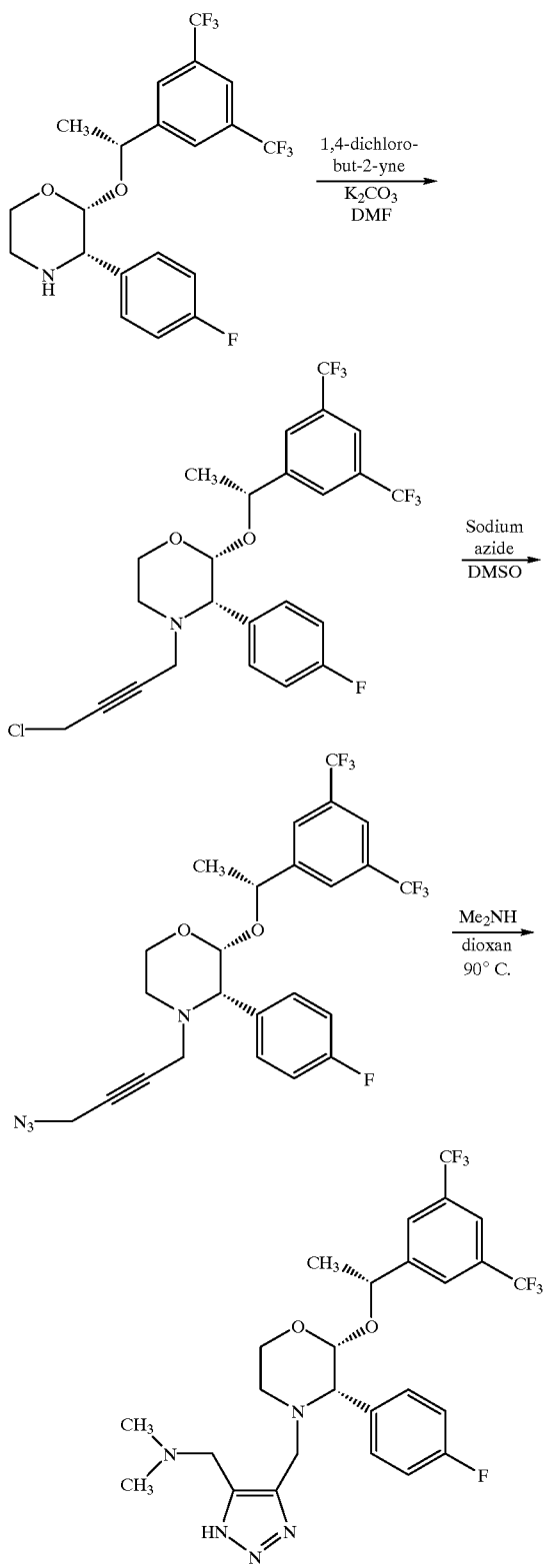

These prior art processes render the synthesis of this compound problematic when attempted on anything other than a laboratory scale. Therefore, there is a need for the development of a process which is readily amenable to scale-up and capable of practical application to a manufacturing plant.

SUMMARY OF THE INVENTION

The present invention is directed to a novel linear process for the preparation of 2-(R)-(1-(R)-(3,5-bis(trifluoromethyl)phenyl)-ethoxy)-4-(5-(dimethylamino)methyl-1,2,3-triazol-4-yl)methyl-3-(S)-(4-fluorophenyl)-morpholine. This compound is a substance P (neurokinin-1) receptor antagonists which is useful in e.g., inflammatory diseases, emesis, depresssion, anxiety, and other neuropsychiatric diseases, including bipolar disorder and schizophrenia.

DETAILED DESCRIPTION OF THE INVENTION

The present invention is directed to linear processes for the preparation of 2-(R)-(1-(R)-(3,5-bis(trifluoromethyl)phenyl)-ethoxy)-4-(5-(dimethylamino)-methyl-1,2,3-triazol-4-yl)methyl-3-(S)-(4-fluorophenyl)-morpholine.

The general process for the preparation of 2-(R)-(1-(R)-(3,5-bis(trifluoromethyl)phenyl)-ethoxy)-4-(5-(dimethylamino)methyl-1,2,3-triazol-4-yl)methyl-3-(S)-(4-fluorophenyl)morpholine is as follows:

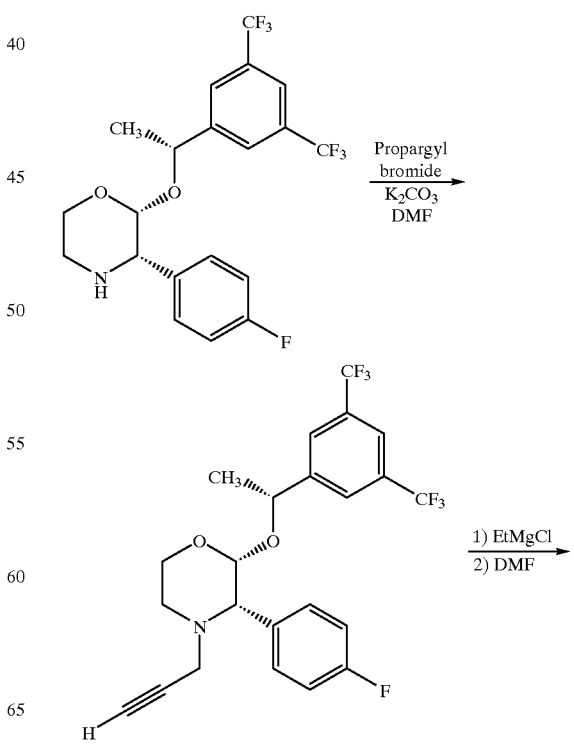

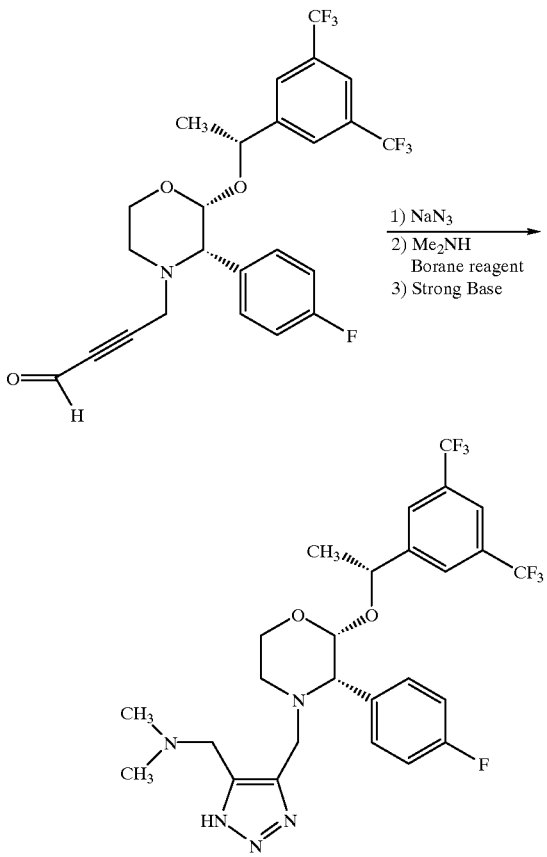

The present invention accordingly provides a convenient, efficient process that provides 2-(R)-(1-(R)-(3,5-bis (trifluoromethyl)-phenyl)-ethoxy)-4-(5-(dimethylamino)-methyl-1,2,3-triazol-4-yl)methyl-3-(S)-(4-fluorophenyl)-morpholine and avoids the need for strenuous reaction conditions or high temperature cyclization.

Thus, in a first aspect of the present invention there is provided a process for the preparation of 2-(R)-(1-(R)-(3,5-bis(trifluoro-methyl) phenyl)-ethoxy)-4-(5-(dimethylamino) methyl-1,2,3 -triazol-4-yl)methyl-3-(S)-(4-fluorophenyl)-morpholine which comprises:

(a) reacting in the presence of a base 2-(R)-(1-(R)-(3,5-bis(trifluoromethyl)phenyl)-ethoxy)-3 -(S)-(4-fluorophenyl)morpholine with an alkylating agent selected from propargyl bromide and propargyl iodide in an organic solvent to give 2-(R)-(1-(R)-(3,5-bis (trifluoromethyl)phenyl)-ethoxy)-3-(S)-(4-fluorophenyl)-4-propargylmorpholine;

(b) reacting 2-(R)-(1-(R)-(3,5-bis(trifluoromethyl) phenyl)-ethoxy)-3-(S)-(4-fluorophenyl)-4-propargylmorpholine in an organic solvent with an organometallic base followed by dimethyl formamide to give 2-(R)-(1-(R)-(3,5-bis(trifluoromethyl)phenyl)-ethoxy)-3-(S)-4-(4-oxo-but-2-ynyl-(4-fluorophenyl)-morpholine;

(c) reacting 2-(R)-(1-(R)-(3,5-bis(trifluoromethyl) phenyl)-ethoxy)-3-(S)-4-(4-oxo-but-2-ynyl-(4-fluorophenyl)morpholine with sodium azide to give 2-(R)-(1-(R)-(3,5 -bis(trifluoro-methyl)phenyl)-ethoxy)-4-(5-oxomethyl-1,2,3-triazol-4-yl)methyl-3-(S)-(4-fluorophenyl)morpholine; and (d) reductive amination of 2-(R)-(1-(R)-(3,5-bis(trifluoromethyl)phenyl)-ethoxy)-4-(5-oxomethyl-1,2,3-triazol-4-yl)methyl-3-(S)-(4-fluorophenyl)morpholine with dimethyl amine to give 2-(R)-(1-(R)-(3,5-bis(trifluoromethyl)phenyl)-ethoxy)-4-(5-(dimethylamino)methyl-1,2,3-triazol-4-yl)methyl-3-(S)-(4-fluorophenyl) morpholine.

In step (a) above, the alkylating agent is preferably propargyl bromide, the base is preferably a weak inorganic base such as potassium carbonate or sodium carbonate, and the organic solvent is preferably dimethylformamide. Step (a) is preferably conducted at room temperature. Preferably the 2-(R)-(1-(R)-(3,5-bis(trifluoromethyl)phenyl)-ethoxy)-3-(S)-(4-fluorophenyl)morpholine of use in step (a) is in the form of its toluene sulfonate salt.

In step (b) above, the organometallic base is selected from Grignard reagents and organolithium reagents. Preferably the organometalic base is selected from ethylmagnesium chloride, n-butyl lithium, methylmagnesium chloride, phenylmagnesium chloride, t-butyl lithium and sec-butyl lithium. Suitable organic solvents of use in the step (b) include an organic solvent selected from the group consisting of: toluene; tetrahydrofuran; xylene (including o-xylene, m-xylene, p-xylene, and mixtures thereof); benzene; petroleum ether; hexane; heptane; cumene; mesitylene; diethyl ether; digylme (2-methoxy-ethyl ether); methyl-t-butyl ether; and the like; and mixtures thereof. In a preferred embodiment, the organic solvent comprises a solvent which is selected from toluene, tetrahydrofuran, and mixtures therof. A suitable temperature for step (b) is in the range of about 0–40° C., preferably about 20–25° C.

In step (c) above, the reaction with sodium azide is conducted in a solvent such as dimethylsulfoxide, toluene, isopropanol, water and mixtures therof.

In step (d) above, reductive amination may be effected by the use of a reducing agent such as: borane-dimethylamine complex; borane-N,N-diethylamine complex; sodium triacetoxyborohydride; sodium borohydride; sodium cyanoborohydride; borane in the presence of an amine base such as triethylamine; borane-t-butylamine complex; borane-N,N-diisopropylethylamine complex; borane-methylsulfide complex; borane-morpholine complex; borane-pyridine complex; borane-tetrahydrofuran complex; borane-triethylamine complex; borane-trimethylamine complex; lithium aluminum hydride; lithium borohydride; lithium triethoxyaluminum hydride; lithium trimethoxyaluminum hydride; and the like. A preferred reducing agent is borane-dimethylamine complex. The reductive amination is generally conducted in the presence of a weak acid such as acetic acid, citric acid, hydrochloric acid. Suitable organic solvents of use in the step (d) include an organic solvent such as dimethylsulfoxide or isopropanol. Optionally, an aqueous solution of a strong base such as an alkali metal hydroxide, for example potassium hydroxide or sodium hydroxide, is added to the reaction mixture following reductive amination to quench the reaction and facilitate work-up.

In an alternate embodiment, the present invention is directed to the compound 2-(R)-(1-(R)-(3,5-bis (trifluoromethyl)phenyl)-ethoxy)-3-(S)-4-(4-oxo-but-2-ynyl-(4-fluorophenyl)morpholine which has the following structure:

In an alternate embodiment, the present invention is directed to the compound 2-(R)-(1-(R)-(3,5-bis(trifluoromethyl)phenyl)-ethoxy)-4-(5-oxomethyl-1,2,3-triazol-4-yl)methyl-3-(S)-(4-fluorophenyl)morpholine which has the following structure:

The preparation of the desired compound with the process of the present invention may be carried out in sequential or convergent synthetic routes. It is noted that in some cases the order of carrying out the subject reactions may be varied to facilitate the reaction or to avoid unwanted reaction products. In general, the process of the present invention is conducted in a sequential manner as presented herein.

NMR spectra were run in $CDCl_3$ and the $^1H$ and $^{13}C$ spectra were measured at 250 and 62.9 MHz. The proton spectra were run with a 10s delay between pulses for the wt % assay. Toluene was dried to less than 150 μg/mL water (by Karl Fisher titration) with 3 Å sieves. Standard inert atmosphere techniques were used for the reaction and work-up.

Many of the starting materials are either commercially available or known in the literature and others can be prepared following literature methods described for analogous compounds. The skills required in carrying out the reaction and purification of the resulting reaction products are known to those in the art. Purification procedures include crystallization, normal phase or reverse phase chromatography.

The most preferred process for the preparation of 2-(R)-(1-(R)-(3,5-bis(trifluoromethyl)phenyl)-ethoxy)-4-(5-(dimethylamino)methyl-1,2,3-triazol-4-yl)methyl-3-(S)-(4-fluorophenyl)morpholine is as follows and is described in detail in the Examples.

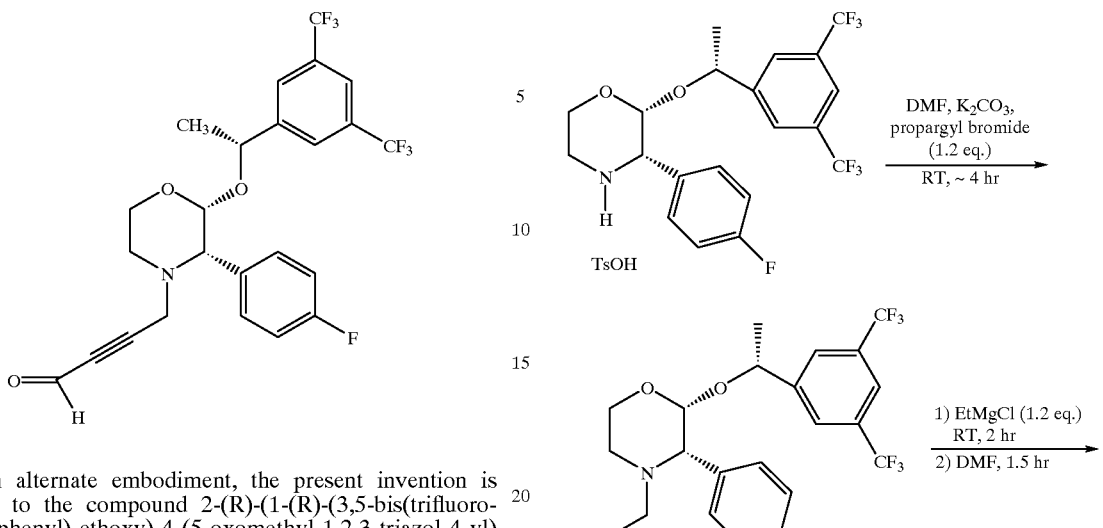

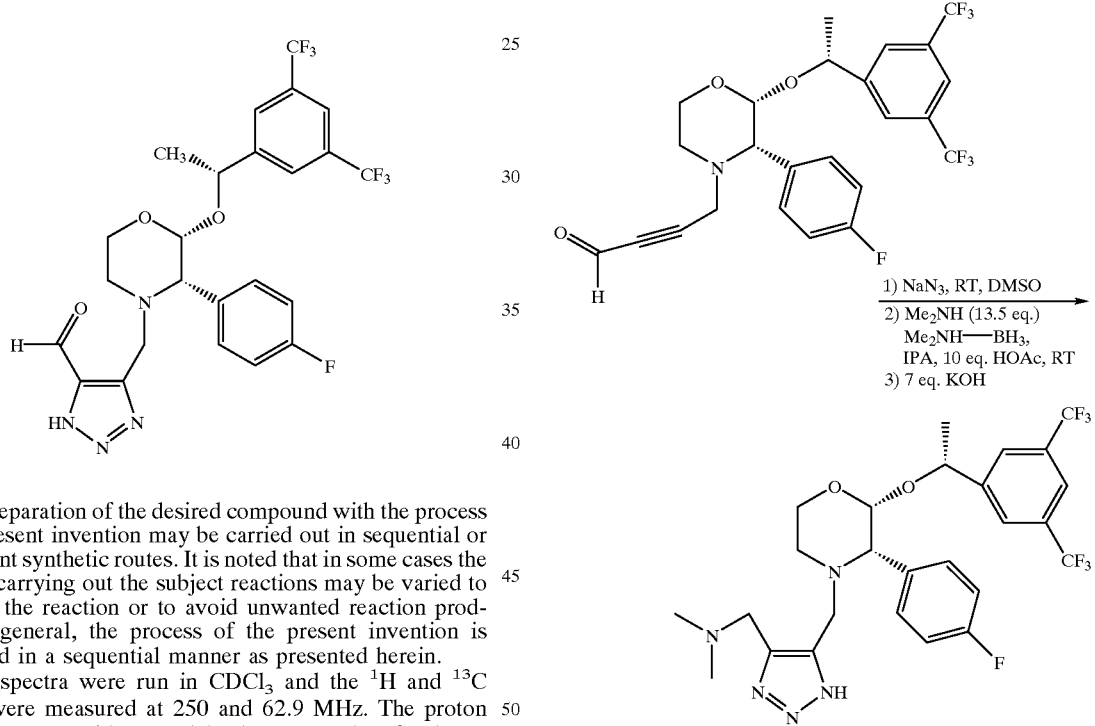

The following examples are provided for the purpose of further illustration only and are not intended to be limitations on the disclosed invention.

EXAMPLE 1

2-(R)-(1-(R)-(3,5-bis(trifluoromethyl)phenyl)-ethoxy)-3-(S)-(4-fluorophenyl)-4-propargylmorpholine

| Materials | Amount | Mol (equiv) |
| --- | --- | --- |
| 2-(R)-(1-(R)-(3,5-bis(trifluoromethyl)-phenyl)ethoxy)-3-(S)-(4-fluorophenyl)-morpholine TsOH salt | 1.83 kg | 3.00 mol (1 eq.) |

-continued

| Materials | Amount | Mol (equiv) |
|---|---|---|
| $K_2CO_3$ | 1.04 kg | 2.5 eq. |
| $BrCH_2CCH$ (80% in toluene) | 535 g | 1.2 eq. |
| $Me_2NH$ | 0.113 L | 0.9 mol |
| DMF | 10 L | |

2-(R)-(1-(R)-(3,5-Bis(trifluoromethyl)phenyl)ethoxy)-3-(S)-(4-fluorophenyl)morpholine TsOH salt (1.83 assay Kg, 3.00 mol) was suspended in 10 L of DMF and potassium carbonate (1.04 Kg, 7.5 mol) was added in one portion to give a white slurry. Propargyl bromide (80 wt % in toluene, 535 g, 3.6 mol) was added dropwise over 30 minutes, the reaction was sligtly exothermic <30° C. (without cooling). The reaction mixture was stirred at room temperature for ~3 hours (~99.9% conversion) and then 40% aqueous dimethylamine was added, and aged for 30 minutes (to destroy excess propargyl bromide), then the reaction solution was partitioned between 20 L of toluene and 20 L of water. The organic layer was washed with water twice (2×18 L). The resulting organic layer was concentrated to 6 L with KF<250 μg/mL (additional toluene may need to be used to achieve this KF specifcation).

EXAMPLE 2
2-(R)-(1-(R)-(3,5-bis(trifluoromethyl)phenyl)-ethoxy)-3-(S)-4-(4-oxo-but-2-ynyl-(4-fluorophenyl)morpholine

| Materials | Amount | Mol (equiv) |
|---|---|---|
| Solution of 2-(R)-(1-(R)-(3,5-bis-(trifluoromethyl)phenyl)ethoxy)-3-(S)-(4-fluorophenyl)-4-propargyl-morpholine | 1.426 kg | 3.00 mol |
| EtMgCl (2.0 M in THF) | 1.88 L | 3.75 mol |
| DMF | 406 mL | 6.00 mol |

To a solution of 2-(R)-(1-(R)-(3,5-bis(trifluoromethyl) phenyl)-ethoxy)-3-(S)-(4-fluorophenyl)-4-propargylmorpholine in toluene at 20–25° C. was added EtMgCl, the reaction was aged for 2 hours, then neat DMF was added at once (can be added over 30 min or 1 hour) and the solution was aged at 20~25° C. for 1.5 hours. Then the solution was quenched into a 5° C. monosodium citrate (5 wt %, 14 L) with toluene (14 L). At the end of the quench, pH should be around 4.2, and organic layer was separated and washed twice with water (14 L). The resulting organic layer was separated and concentrated and optionally solvent switched to DMSO (6 L) to yield a solution of 2-(R)-(1-(R)-(3,5-bis(trifluoromethyl)phenyl)-ethoxy)-3-(S)-4-(4-oxo-but-2-ynyl-($^4$-fluorophenyl)morpholine.

EXAMPLE 3
2-(R)-(1-(R)-(3,5-bis(trifluoromethyl)phenyl)-ethoxy)-4-(5-(dimethylamino) methyl-1,2,3-triazol-4-yl)methyl-3-(S)-(4-fluorophenyl)morpholine

| Materials | Amount | Mol (equiv) |
|---|---|---|
| $NaN_3$ | 0.293 Kg | 4.5 mol |
| DMSO | 15 L (total) | |
| 40% Dimethylamine | 5.0 L | 40 mol |

-continued

| Materials | Amount | Mol (equiv) |
|---|---|---|
| Borane dimethylamine | 177 g | 3.0 mol |
| HOAc | 1.71 L | 30 mol |
| IPA | 2.5 L | |
| 45% KOH | 2.62 Kg | 21 mol |

To a suspension of $NaN_3$ in DMSO (9 L) (or optionally in toluene) at 20–25° C. was added a solution of 2-(R)-(1-(R)-(3,5-bis(trifluoromethyl) phenyl)-ethoxy)-3-(S)-4-(4-oxo-but-2-ynyl-(4-fluorophenyl)morpholine in DMSO (6 L) over a period of time (longer time for addition is better, for this scale reaction it took 30 minutes the addition). After the addition, the reaction was aged at 20–25° C. for 30 minutes, then the solution was diluted with 40 wt % aqueous dimethylamine, followed by addition of IPA, acetic acid and borane dimethylamine complex. The resulting solution was stirred at 40° C. for 4 hours, then 45% KOH was added and continued for another 4 hours. The reaction solution was diluted with water (15 L), added 15 L heptane then neutralized with concentrated $H_3PO_4$ to pH around 8.5~9.0, then added additional heptane (5 L) and ethyl acetate (5 L), and organic layer was separated and washed twice with water (15 L). Optionally, toluene may be used for extraction. The resulting organic layer was concentrated to give 2-(R)-(1-(R)-(3,5-bis (trifluoro-methyl)phenyl)-ethoxy)-4-(5-(dimethylamino)methyl-1,2,3-triazol-4-yl)methyl-3-(S)-(4-fluorophenyl)morpholine.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, reaction conditions other than the particular conditions as set forth herein above may be applicable as a consequence of variations in the reagents or methodology to prepare the compounds from the processes of the invention indicated above. Likewise, the specific reactivity of starting materials may vary according to and depending upon the particular substituents present or the conditions of manufacture, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A process for the preparation of 2-(R)-(1-(R)-(3,5-bis (trifluoro-methyl)phenyl)-ethoxy)-4-(5-(dimethylamino) methyl-1,2,3-triazol-4-yl)methyl-3-(S)-(4-fluorophenyl)-morpholine which comprises:
   (a) reacting in the presence of a base 2-(R)-(1-(R)-(3,5-bis(trifluoromethyl)phenyl)-ethoxy)-3-(S)-(4-fluorophenyl)morpholine with an alkylating agent selected from propargyl bromide and propargyl iodide in an organic solvent to give 2-(R)-(1-(R)-(3,5-bis (trifluoromethyl)phenyl)-ethoxy)-3-(S)-(4-fluorophenyl)-4-propargylmorpholine;
   (b) reacting 2-(R)-(1-(R)-(3,5-bis(trifluoromethyl) phenyl)-ethoxy)-3-(S)-(4-fluorophenyl)-4-propargylmorpholine in an organic solvent with an organometallic base followed by dimethyl formamide to give 2-(R)-(1-(R)-(3,5-bis(trifluoromethyl)phenyl)-ethoxy)-3-(S)-4-(4-oxo-but-2-ynyl-(4-fluorophenyl) morpholine;

(c) reacting 2-(R)-(1-(R)-(3,5-bis(trifluoromethyl) phenyl)-ethoxy)-3-(S)-4-(4-oxo-but-2-ynyl-(4-fluorophenyl)morpholine with sodium azide to give 2-(R)-(1-(R)-(3,5-bis(trifluoro-methyl)phenyl)-ethoxy)-4-(5-oxomethyl-1,2,3-triazol-4-yl)methyl-3-(S)-(4-fluorophenyl)morpholine; and (d) reductive amination of 2-(R)-(1-(R)-(3,5-bis(trifluoro-methyl)phenyl)-ethoxy)-4-(5-oxomethyl-1,2,3-triazol-4-yl)methyl-3-(S)-(4-fluorophenyl) morpholine with dimethyl amine to give 2-(R)-(1-(R)-(3,5-bis(trifluoro-methyl)phenyl)-ethoxy)-4-(5-(dimethylamino)methyl-1,2,3-triazol-4-yl)methyl-3-(S)-(4-fluorophenyl)morpholine.

2. The process of claim 1 wherein step (a) the alkylating agent is propargyl bromide.

3. The process of claim 2 wherein step (a) the base is potassium carbonate.

4. The process of claim 3 wherein step (a) the solvent is dimethylformamide.

5. The process of claim 1 wherein step (b) the organometallic base is ethylmagnesium chloride.

6. The process of claim 5 wherein step (b) the organic solvent comprises a solvent which is selected from toluene, tetrahydrofuran, and mixtures therof.

7. The process of claim 1 wherein step (c) the reaction with sodium azide is conducted in a solvent selected from: dimethylsulfoxide, toluene, isopropanol, water and mixtures therof.

8. The process of claim 1 wherein step (d) the reductive amination is conducted with a reducing agent which is borane-dimethylamine complex.

9. The process of claim 8 wherein step (d) the reductive amination is conducted in the presence of acetic acid.

10. The process of claim 9 wherein step (d) an aqueous solution of potassium hydroxide is added to the reaction mixture following the reductive amination.

11. A process for the preparation of 2-(R)-(1-(R)-(3,5-bis(trifluoro-methyl)phenyl)-ethoxy)-4-(5-(dimethylamino)methyl-1,2,3-triazol-4-yl)methyl-3-(S)-(4-fluorophenyl)-morpholine which comprises:

reductive amination of 2-(R)-(1-(R)-(3,5-bis(trifluoro-methyl) phenyl)-ethoxy)-4-(5-oxomethyl-1,2,3-triazol-4-yl)methyl-3-(S)-(4-fluorophenyl)morpholine with dimethyl amine to give 2-(R)-(1-(R)-(3,5-bis(trifluoro-methyl)phenyl)-ethoxy)-4-(5-(dimethylamino)methyl-1,2,3-triazol-4-yl)methyl-3-(S)-(4-fluorophenyl) morpholine.

12. The process of claim 11 wherein the reductive amination is conducted with a reducing agent which is borane-dimethylamine complex.

13. The process of claim 12 wherein the reductive amination is conducted in the presence of acetic acid.

14. The process of claim 13 wherein an aqueous solution of potassium hydroxide is added to the reaction mixture following the reductive amination.

15. A compound which is 2-(R)-(1-(R)-(3,5-bis (trifluoro-methyl)phenyl)ethoxy)-3-(S)-4-(4-oxo-but-2-ynyl-(4-fluorophenyl)-morpholine.

16. A compound which is 2-(R)-(1-(R)-(3,5-bis (trifluoro-methyl)phenyl)ethoxy)-4-(5-oxomethyl-1,2,3-triazol-4-yl) methyl-3-(S)-(4-fluorophenyl)morpholine.

* * * * *